United States Patent

Vidlund et al.

[11] Patent Number: 6,033,394
[45] Date of Patent: Mar. 7, 2000

[54] CATHETER SUPPORT STRUCTURE

[75] Inventors: Robert M. Vidlund, Maplewood; Daniel J. Klima, Plymouth, both of Minn.

[73] Assignee: Intratherapeutics, Inc., St. Paul, Minn.

[21] Appl. No.: 08/985,810

[22] Filed: Dec. 5, 1997

[51] Int. Cl.[7] .......................... A61M 25/00; A61M 5/00; A61M 29/00; F16L 9/00
[52] U.S. Cl. .................. 604/524; 604/524; 604/526; 604/264; 606/194; 138/172
[58] Field of Search ..................... 604/280, 282, 604/264, 281, 523–28, 533, 534; 138/123, 124, 125, 127, 137, 138, 140, 141, 143, 145, 146, 153, 144, 172; 606/194, 198

[56] References Cited

U.S. PATENT DOCUMENTS

| | | | |
|---|---|---|---|
| 5,702,373 | 12/1997 | Samson | 604/526 |
| 5,795,341 | 8/1998 | Samson | 604/526 |
| 5,827,242 | 10/1998 | Follmer et al. | 604/526 |
| 5,843,168 | 12/1998 | Dang | 606/194 |
| 5,846,246 | 12/1998 | Dirks et al. | 606/194 |
| 5,849,034 | 12/1998 | Schwartz | 606/194 |
| 5,868,782 | 2/1999 | Frantzen | 606/194 |
| 5,868,783 | 2/1999 | Tower | 606/194 |
| 5,891,108 | 4/1999 | Leone et al. | 604/264 |

FOREIGN PATENT DOCUMENTS

| | | |
|---|---|---|
| 0 369 383 | 5/1990 | European Pat. Off. . |
| 0 692 276 A2 | 1/1996 | European Pat. Off. . |
| WO 96/28208 | 9/1996 | WIPO . |
| WO 96/33763 | 10/1996 | WIPO . |
| WO 96/38193 | 12/1996 | WIPO . |

*Primary Examiner*—Ronald Stright, Jr.
*Assistant Examiner*—Patricia Bianco
*Attorney, Agent, or Firm*—Merchant & Gould P.C.

[57] ABSTRACT

A catheter has a support segment which includes a plurality of support struts. Each of the struts has first and second ends longitudinally spaced apart along a longitudinal axis of the segment. The struts curve at least partially around the axis from the first ends to the second ends. The support struts include a first set and a second set. The struts of the first set extend around the axis in a clockwise direction. The struts of the second set extend around the axis in a counter-clockwise direction.

15 Claims, 2 Drawing Sheets

CATHETER SUPPORT STRUCTURE

BACKGROUND OF THE INVENTION

1. Field of the Invention

This invention pertains to catheters for passage through a vasculature system. More particularly, this invention pertains to a novel construction of at least a segment of a catheter.

2. Description of the Prior Art

Catheters are widely used in medical treatment. A catheter is an elongated flexible member advanced through the vasculature system to a desired site. The catheter may be advanced over a previously inserted guide wire.

With the catheter in place, a wide variety of substances may be passed through the catheter to the site. For example, drugs may be moved through the catheter for site-specific drug delivery. Also, implements may be passed through the catheter. The catheter may also be used to remove fluids from the site. Still further, a catheter may be equipped with implements (e.g., balloon tips) for performing procedures (e.g., angioplasty) at the site.

Catheters have long been used in cardiovascular treatment. More recently, catheters are used in neurological procedures requiring advancement of the catheter through very narrow vessels. To accomplish these advances, a high degree of flexibility is desired. Also, catheters need very thin walls in order to retain an internal bore having as large a diameter as possible.

While advancing a catheter, a physician may twist a proximal end of the catheter in order to cause a corresponding twist of the distal end of the catheter (referred to as "torque transmission response"). A consistently reliable torque transmission response (e.g., a consistent one-to-one torque transmission response) is desired.

In designing catheters, it is desirable to provide a catheter which is kink resistant. Namely, a catheter typically is a tube with an internal bore of circular cross-section. When a catheter bends, it may be inclined to kink resulting in closure or geometric deformation of the circular bore. Such closure or deformation is undesirable. Further, in certain applications, the catheter may be subjected to high internal pressures (e.g., 300 psi). Such pressures tend to burst the catheter or expand the catheter geometry.

Catheter geometry can also by deformed by torque applied to the catheter. Many catheters are designed to have a reinforcing coil extending along the length of the catheter. If torque is applied in the direction of the coil winding, the internal diameter of the catheter may reduce. If torque is applied in the opposite direction, the diameter may expand. Dual coil catheters (i.e., catheters having two coils extending the length of the catheter with one coil being a clockwise wind and the other being a counter-clockwise wind) have been developed to retain dimensional stability regardless of direction of torque and to increase torque transmission. Unfortunately, such catheters are costly and have an extra layer of coil which takes up an already limited space within the vasculature.

SUMMARY OF THE INVENTION

According to a preferred embodiment of the present invention, a catheter is disclosed having a segment which comprises a plurality of support struts. Each of the struts has first and second ends longitudinally spaced apart along a longitudinal axis of the segment. The struts extend at least partially around the axis from the first ends to the second ends. The support struts include a first set and a second set. The struts of the first set extend around the axis in a clockwise direction relative to a first end of the segment. The struts of the second set extend around the axis in a counter-clockwise direction.

DESCRIPTION OF THE PREFERRED EMBODIMENT

Referring now to the several drawing figures in which identical elements are numbered identically throughout, a description of a preferred embodiment of the present invention will now be provided.

Figure 1:
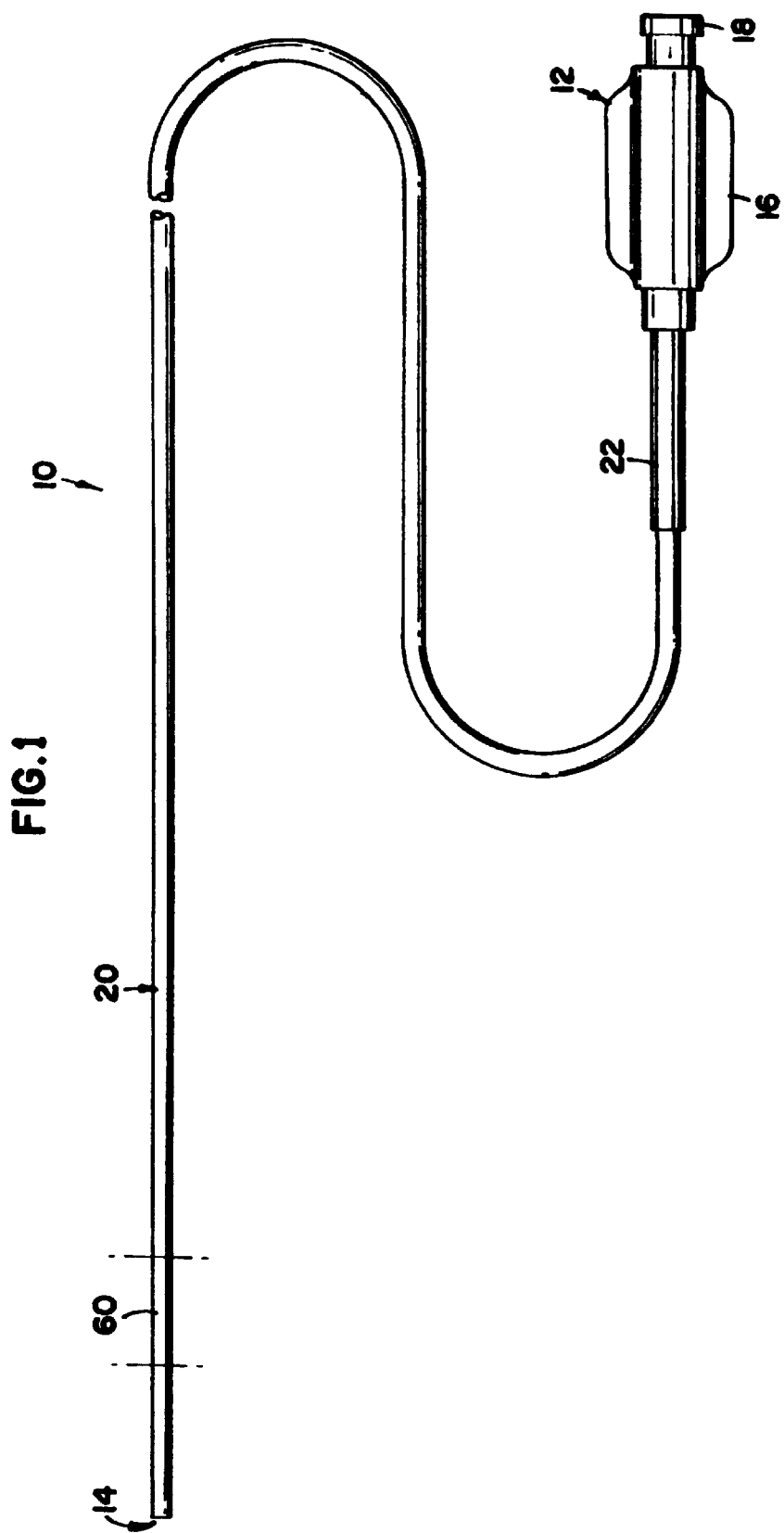
FIG. 1 is an overall view of a catheter according to the present invention.

FIG. 1 illustrates a catheter 10. The catheter 10 extends from a proximal end 12 to a distal end 14. At the proximal end 12, a hub 16 is provided to be gripped by a physician as well as having an inlet 18 for injection of fluids into the catheter 10. A flexible hollow shaft 20 is connected to the hub 16. The shaft 20 is sized to be inserted into a patient's vasculature. The shaft 20 is commonly about 150 cm long. A strain relief jacket 22 connects the shaft 20 to the hub 16. The foregoing description forms no part of this invention and is given to facilitate an understanding of the present invention.

The catheter 10 includes a segment 60 having the novel construction of the present invention. (For purposes of the remainder of this description, the word "catheter" is generally used to refer to the flexible shaft 20 of FIG. 1 having the segment 60 which a construction as will be described.) While the entire length of the catheter 10 can be constructed as will be described with reference to segment 60, it may be desirable to have a catheter 10 of multiple segments of different construction to impart different properties to different regions of the catheter 10 along its length. For example, it may be desirable to provide a catheter 10 having a proximal portion stiffer than a more flexible distal portion. While the present invention is suitable for forming catheter segments of varying degrees of flexibility and other properties, the present invention is described with reference to a segment 60 of the length of the catheter 10. This is to allow for catheters where the entire length is constructed according to the teachings of this application as well as catheters where only a discrete portion is so constructed and where the remainder is constructed according to conventional catheter construction techniques.

Figure 2:
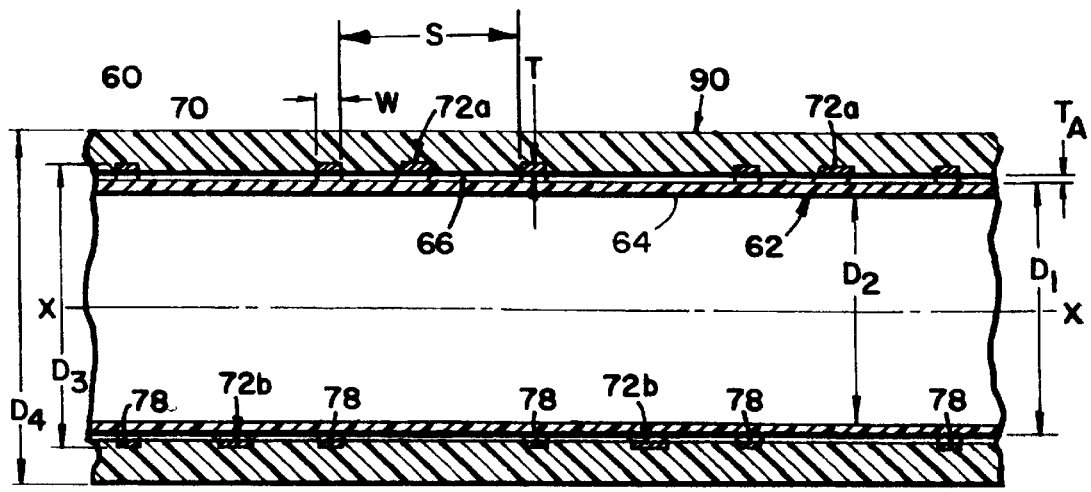
FIG. 2 is a cross-sectional, longitudinal view of a longitudinal segment of the catheter of FIG. 1.
Figure 3:
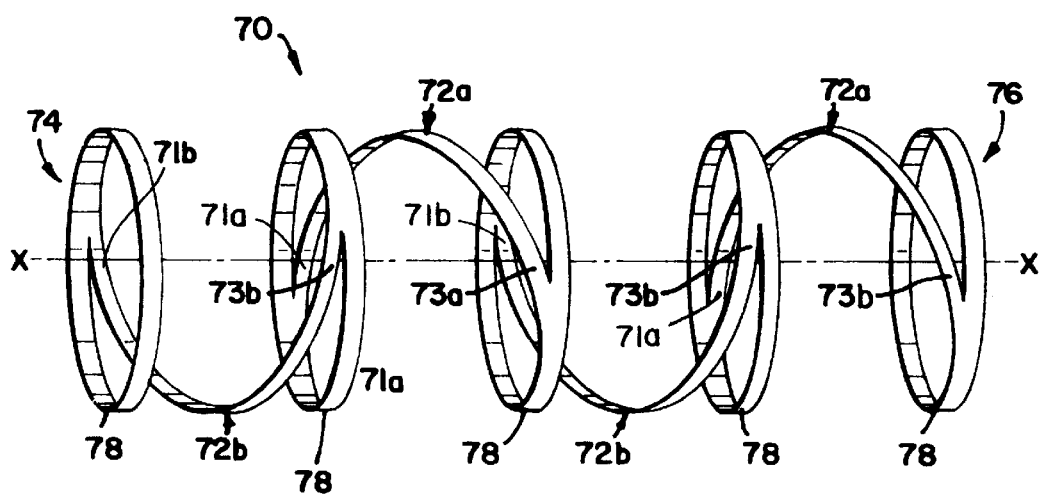
FIG. 3 is a perspective view of a support structure of the segment of FIG. 2.

With reference to FIGS. 2 and 3, the segment 60 is shown to illustrate the novel construction. The segment 60 is a multi-layer construction including a flexible inner layer 62. By way of non-limiting example, the inner layer 62 is polytetraflouroethylene (PTFE) more commonly known by the trademark Teflon™. In a preferred embodiment, layer 62 has an outer diameter $D_1$ of 0.0230 inch (0.58 mm) and an inner diameter $D_2$ of 0.0210 inch (0.53 mm) to define an internal bore 64 surrounded by the Teflon inner tube layer 62.

The segment 60 also includes a novel support structure 70 as will be more fully described. The support structure 70 is generally tubular and is adhered to the external surface of the inner layer 62 by a thin bonding layer of any suitable adhesive 66 (e.g., polyurethane having a thickness $T_A$ of about 0.0004 inch or 0.01 mm). The support structure 70 has an outer diameter $D_3$ of about 0.025 inch (0.635 mm).

Surrounding the exterior of the support structure 70, an outer polymer jacket 90 is provided. The outer jacket 90 may be any suitable flexible material for use in the vascular system. Such materials may be nylon or urethane. The outer jacket 90 has an outer diameter $D_4$ of 0.029 inch (0.74 mm).

In the foregoing, Applicants have provided a specific description of various layers of segment 60 as well as describing specific materials and dimensions. Such specificity has been given to describe a preferred embodiment of a specific catheter 10 utilizing the novel support structure 70 as will be described. More or fewer layers of materials could be used with structure 70 to impart desired properties (i.e., varying stiffness, strength, etc.) to segment 60. Similarly, specific materials and dimensions may be varied to alter the properties of segment 60.

Referring now to FIG. 3, the novel support structure 70 of the present invention will now be described. The support structure 70 includes a plurality of helical support struts 72a, 72b. As will become apparent, the plurality of support struts includes first and second sets of struts. Struts of the first set are designated 72a while struts of the second set are designated 72b.

While having an open structure, support structure 70 is generally tubular and extends from a first end 74 to a second end 76. The support structure 70 surrounds the longitudinal axis X-X. As indicated, the length of the support structure 70 (e.g., the distance between ends 74, 76) may be the entire length of the catheter or only a portion of the entire length.

Each of the struts 72a, 72b extends from a first end 71a, 71b to a second end 73a, 73b. The first and second ends 71a, 73a and 71b, 73b of a strut 72a, 72b are spaced apart longitudinally with respect to axis X-X. Additionally, each of the struts 72a, 72b curves around the axis X-X between ends 71a, 73a and 71b, 73b. In the preferred embodiment shown in the figures, the struts 72a, 72b are helical about axis X-X and curve substantially 360° about axis X-X.

Viewed from the first end 74 of the support structure 70, the struts 72a curve about axis X-X in a clockwise direction. Struts 72b curve in an opposite counter-clockwise direction.

In the embodiment shown, the struts 72a alternate in series with struts 72b along the length of the support structure 70. Adjacent ends 73a, 71b and 71a, 73b of adjacent struts 72a, 72b are connected such that all struts 72a, 72b along the length of support structure 70 are interconnected.

In the embodiment shown, a plurality of circumferential cylindrical rings or supports 78 are disposed between each of adjacent struts 72a, 72b. Accordingly, the adjacent ends 73a, 71b and 71a, 73b are not directly interconnected but, instead, are connected to opposite ends of a common circumferential support 78.

By way of example, the circumferential supports 78 and the struts 72a, 72b have a width W of about 0.003 inch (0.076 mm). In the case of circumferential supports 78, the width is the dimension parallel to the axis X-X. In the case of the struts 72a, 72b, the width is the dimension transverse to the helical path of the struts 72a, 72b. The circumferential supports 78 and the struts 72a, 72b have a thickness T of about 0.001 inch (0.025 mm) (i.e., the radial dimension measured between the inner and outer diameters of the circumferential supports 78 and the struts 72a, 72b). Finally, the circumferential supports 78 have an axial spacing S between opposing/adjacent supports 78 of about 0.005 inch (0.127 mm).

Preferably, the support structure 70 is fabricated from a solid blank of medical grade stainless steel tubing such that after such fabrication the supports 78 and struts 72a, 72b are integrally and continuously formed of uninterrupted metal. Other possible materials includes nickel-titanium alloys (e.g., nitinol) and cobalt-chromium-nickel alloys (e.g., Elgiloy™ alloy of Elgiloy, Inc. of Elgin, Ill., U.S.A.). Such a fabrication process includes starting with a rod (not shown) having an outer diameter equal to the desired inner diameter of the PTTE layer 62. The PTFE layer 62 is placed over the rod which acts as a jig to hold the elements of catheter 10 during fabrication. The adhesive 66 is applied to the external surface of PTFE layer 62. A solid tube of medical grade stainless steel (referred to as a hypotube) is then adhered to PTFE layer 62 by adhesive 66. As an alternative, the PTFE layer 62 and the metal tube can be assembled without the adhesive 66 with parts held in alignment until the final outer layer 90 is applied.

The solid metal tube is then milled to remove excess material of the tube as waste and leaving only the material of the circumferential supports 78 and the struts 72a, 72b as the support structure 70. In a preferred embodiment, the metal tube is milled by a chemical milling process. In such a process, a pattern mask of the desired pattern of the circumferential supports 78 and struts 72a, 72b is placed over the metal tube. A light source sensitizes a photoresist applied to the metal to create a pattern on the metal tube matching the mask. The photo-sensitized tube is then chemically etched to dissolve away the areas of the tube corresponding to the waste leaving only the desired material of the circumferential supports 78 and struts 72a, 72b. It will be appreciated that this description of a chemical milling of the metal tube forms no part of this invention per se. Such a process is more fully described in commonly assigned and copending U.S. patent application Ser. No. 08/645,607 the specification of which was published on Dec. 5, 1996 as International Publication No. WO96/38193 on PCT International application Ser. No. PCT/US96/08232.

After the tube is so milled, the outer layer 90 is applied to the outer surface of the support structure 70. The material of the outer layer 90 may, at the option of a designer, fill in the axial spacing S between the circumferential supports 78 or leave such spacing as voids to enhance flexibility. The rod is then removed from the PTFE layer 62 leaving a completed segment 60.

Having described the structure and fabrication of the catheter segment 60 in a preferred embodiment, the benefits of the present invention will be apparent to one of ordinary skill in the art. The present invention overcomes the disadvantage of prior art coil-construction catheters. Namely, in the case of a catheter formed with a single counter-clockwise coil (such as that shown in U.S. Pat. No. 5,178,158), such catheters would tend toward expansion or contraction in response to a clockwise or counter-clockwise torque, respectively, applied to the catheter. In addition to being urged to geometric deformation, such catheters would have a less reliable torque transmission response since at least a portion of the torque energy is wasted in geometric deformation.

With the present invention, the combination of clockwise and counter-clockwise helical support struts result in the clockwise struts 72a and the counter-clockwise struts 72b urging toward expansion and contraction, respectively, in response to a counter-clockwise application of torque. As a result, the expansion and contraction forces tend to counteract each other resulting in enhanced geometric integrity and enhanced torque transmission response.

The prior art has used multiple coils for improving clockwise and counter-clockwise torque response as well as counter-acting expansion and contraction forces. Such designs apply an outer coil layer (e.g., a clockwise coil) surrounding an inner coil layer (e.g., a counter-clockwise coil). While such designs improve torque responsiveness, torque transmission responsiveness varies between clockwise and counter-clockwise applications of torque. Further, such designs have the added disadvantage of an additional layer of construction. In certain applications (e.g., neurological catheters), a thin wall catheter is a significant design constraint due to the extremely small vessels through which the catheter is to pass and the desire to maximize the diameter of the internal bore of the catheter and to make the catheter extremely flexible. In the present invention, the clockwise and counter-clockwise helical struts 72a, 72b reside in the same layer and have the same diameters.

The present invention also permits incorporation of the circumferential supports 78. These rings 78 increase the burst strength of the catheter 10 when used to infuse drugs or other media at high pressure (i.e., 300 psi). The rings 78 are reinforcing members resisting radial expansion forces urging the catheter toward expansion. Further, the rings 78 resist geometric deformation of the internal cross-section of the catheter 10 at the rings 78. Further, the benefits of the rings 78 are achieved in a design without needing an additional layer of material to accommodate the rings 78. Namely, the rings 78 reside in the same layer and have the same diameters as the support struts 72a, 72b.

The present invention has been described in a preferred embodiment and may be modified while keeping with the teachings of the present invention. For example, the support structure 70 need not be formed of metal or fabricated in the chemical milling manner indicated. The support structure 70 can be formed from any structural material in any manner including, without limitation, electrical discharge machining, laser cutting, or assembly of individual components.

Similarly, while a preferred support structure 70 has been disclosed, numerous modifications can be made to the structure to vary the properties of the catheter 10 to meet design objectives for a specific application. For example, cicumferential support rings 78 can be omitted where burst strength is not an issue (in which case, the struts 72a, 72b are directly interconnected). The geometry of the support rings can be varied (e.g., thicker, wider, narrower, closer or more distant spacing as well as nonsymmetrical shapes compared to the symmetrical shapes shown) to vary strength and flexibility. While the helical struts 72a, 72b are shown in an alternating series, such an arrangement can be modified (e.g., a series of multiple clockwise struts 72a followed by one or a series of multiple counter-clockwise struts 72b or other such variations in the pattern of the series of struts 72) to control torque transmission response or stiffness. The shape of the helical struts 72 can be modified. For example, the tightness of the coiling of the struts, the amount of bending of the struts (i.g., greater or less than the 360° bending shown per strut 72a, 72b) can be modified to control the torque transmission response as well as the stiffness of the catheter. Also, the relative positioning of the connected ends (e.g., ends 71b and 73a) of adjacent struts 72a, 72b can be varied. For example, in FIG. 3, the ends 71b and 73a are positioned on diametrically opposite sides of a ring 78. The ends 71b and 73a could be positioned in direct opposition on a ring 78 or any other relative positioning to control stiffness of the catheter.

From the foregoing, the present invention has been disclosed in a preferred embodiment. The invention permits construction of a catheter overcoming disadvantages of prior designs as well as providing a structure having various features which can be modified to design catheters with optimum performance for a wide variety of applications. It is intended that modifications and equivalents of the disclosed concepts, such as those which readily occur to one of skill in the art shall be included within the scope of the claims appended hereto.

What is claimed is:

1. A catheter having a longitudinal axis, said catheter comprising:

a flexible hollow shaft having a distal end and a proximal end, said distal end sized to be inserted into a patient's body lumen;

said shaft including at least a segment having:

A. a flexible tubular layer having an inner lumen with said tubular layer enclosing said catheter lumen;

B. a support structure secured to said layer for maintaining said inner lumen and for transmitting forces along a length of said segment, said support structure including:

(a) a plurality of support struts each having first and second ends longitudinally spaced apart along said axis, said struts extending at least partially around said axis from said first ends to said second ends;

(b) said plurality of support struts including a first set of said struts and a second set of said struts;

(c) said struts of said first set curving around said axis in a clockwise direction relative to a first end of said segment;

(d) said struts of said second set curving around said axis in a counter-clockwise direction relative to said first end of said segment; and (e) said struts of said first and second sets disposed in a common radial layer spaced from said axis.

2. A catheter according to claim 1 wherein at least one of said struts curves around said axis more then 0°.

3. A catheter according to claim 2 wherein said at least one of said struts curves around said axis less than 360°.

4. A catheter according to claim 1 wherein said struts of said first set are connected to said struts of said second set.

5. A catheter according to claim 1 wherein said struts are linearly aligned along said longitudinal axis.

6. A catheter according to claim 1 wherein said struts of said first set and said struts of said second set are interspersed along said longitudinal axis.

7. A catheter according to claim 1 wherein said struts of said first set and said struts of said second set are sequentially aligned along said longitudinal axis.

8. A catheter according to claim 1 wherein said struts of said first set and said struts of said second set are alternated along said longitudinal axis.

9. A catheter according to claim comprising a plurality of circumferential supports surrounding said axis and spaced along said longitudinal dimension.

10. A catheter according to claim 1 wherein said circumferential supports are interconnected by said struts.

11. A catheter according to claim 1 wherein said struts are disposed surrounding an external surface of an elongated inner layer.

12. A catheter according to claim 1 wherein said support struts are helical.

13. A catheter according to claim 1 wherein said segment is sized to fit within a blood vessel.

14. A catheter according to claim 1 wherein said segment further includes an inner layer of flexible material surrounded by said support struts and said flexible layer is an outer layer of flexible material surrounding said support struts, said inner layer having an inner surface defining a catheter bore.

15. A catheter according to claim 1 further wherein said flexible layer is a flexible outer layer surrounding on outer surface of said struts.

* * * * *